United States Patent
Ikebe et al.

(10) Patent No.: US 8,992,955 B2
(45) Date of Patent: Mar. 31, 2015

(54) OIL-IN-WATER EMULSION COMPOSITION

(75) Inventors: Yosuke Ikebe, Kanagawa (JP); Yuko Nagare, Kanagawa (JP)

(73) Assignee: Shiseido Company, Ltd., Tokyo (JP)

( * ) Notice: Subject to any disclaimer, the term of this patent is extended or adjusted under 35 U.S.C. 154(b) by 54 days.

(21) Appl. No.: 13/258,009

(22) PCT Filed: Mar. 26, 2010

(86) PCT No.: PCT/JP2010/055367
§ 371 (c)(1),
(2), (4) Date: Nov. 8, 2011

(87) PCT Pub. No.: WO2010/113795
PCT Pub. Date: Oct. 7, 2010

(65) Prior Publication Data
US 2012/0045403 A1 Feb. 23, 2012

(30) Foreign Application Priority Data

Mar. 30, 2009 (JP) .................. 2009-081753
Mar. 25, 2010 (JP) .................. 2010-070278

(51) Int. Cl.
*A61Q 17/04* (2006.01)
*A61Q 1/00* (2006.01)
*A61K 8/06* (2006.01)
*A61K 8/894* (2006.01)

(52) U.S. Cl.
CPC ............... *A61Q 17/04* (2013.01); *A61K 8/062* (2013.01); *A61K 8/894* (2013.01)
USPC ............................................ 424/401; 424/59

(58) Field of Classification Search
None
See application file for complete search history.

(56) References Cited

U.S. PATENT DOCUMENTS

| 7,276,553 | B2 * | 10/2007 | Garrison et al. ............... 524/588 |
| 2005/0228056 | A1 | 10/2005 | Asai et al. |
| 2007/0207176 | A1 | 9/2007 | Kamei et al. |
| 2007/0218021 | A1 * | 9/2007 | Wells ............................... 424/59 |
| 2009/0035236 | A1 * | 2/2009 | Maes et al. ...................... 424/59 |
| 2009/0041694 | A1 * | 2/2009 | Pinzer et al. ..................... 424/63 |
| 2010/0112017 | A1 | 5/2010 | Mizutani et al. |

FOREIGN PATENT DOCUMENTS

| EP | 0568102 | * | 11/1993 |
| JP | WO2004/006871 A1 | | 1/2004 |
| JP | 2007-238645 A | | 9/2007 |
| JP | 2007238645 | | 9/2007 |
| JP | 2007277142 | | 10/2007 |
| JP | 2008031045 | | 2/2008 |
| JP | 2008-069115 A | | 3/2008 |
| JP | 2008069115 | | 3/2008 |
| JP | A-2010-254673 | | 11/2010 |
| JP | B-4854051 | | 11/2011 |
| WO | WO 2004006871 | | 1/2004 |
| WO | WO 2010/113795 | | 10/2010 |

OTHER PUBLICATIONS

PEG/PPG-19/19 dimethicone in Chemical Book (Jan. 2013).*
Dow Corning BY 11-030 Product Information (May 2011).*
Japanese Office Search Report for PCT/JP2010/055367 filed Mar. 26, 2010, (both JP and English 4 pages).
Notice of Reasons for Rejection from JPO, Dated Jun. 17, 2010, for JP Parent Patent Application No. JP2010-070278 (Full JP, Full English and certification of translation).
Written Arguments to JPO, dated Aug. 16, 2010, for JP Parent Patent Application No. JP2010-070278 (Full JP, Full English and certification of translation).
Written Amendments to JPO, dated Aug. 16, 2010, for JP Parent Patent Application No. JP2010-070278 (Full JP, Full English and certification of translation).
Decision of rejection from JPO, Dated Jan. 4, 2011, for JP Parent Patent Application No. JP2010-070278 (Full JP, Full English and certification of translation).
Notice of Appeal and Appeal Brief to JPO, dated Apr. 4, 2011, for JP Parent Patent Application No. JP2010-070278 (Full JP, Full English and certification of translation).
Notice of Reasons for Rejection (Appeal Stage) from JPO, dated Sep. 2, 2011, for JP Parent Patent Application No. JP2010-070278 (Full JP, Full English and certification of translation).
Written Arguments (Appeal Stage) to JPO, dated Sep. 16, 2011, for JP Parent Patent Application No. JP2010-070278 (Full JP, Full English and certification of translation).
Written Amendments (Appeal Stage) to JPO, dated Sep. 16, 2011, for JP Parent Patent Application No. JP2010-070278 (Full JP, Full English and certification of translation).
Appeal Decision from JPO, Dated Oct. 2, 2011, for JP Parent Patent Application No. JP2010-070278 (Full JP, Full English and certification of translation).

* cited by examiner

*Primary Examiner* — Jyothsna Venkat
(74) *Attorney, Agent, or Firm* — Andrew F. Young, Esq.; Lackenbach Siegel, LLP

(57) ABSTRACT

Disclosed is an oil-in-water emulsion base which is stable even when ethanol in an amount of 50% by mass or less is blended therein and which exhibits excellent water resistance after being applied to the skin or the like. Specifically disclosed is an oil-in-water emulsified cosmetic composition which is characterized by containing (A) 0.1-10% by mass of a polyether-modified silicone having an HLB(Si) of 5-10, (B) 5-50% by mass of ethanol, (C) 0.01-3% by mass of a hydrophilic thickening agent and (D) 0.1-15% by mass of a polyol. Preferably, the oil-in-water emulsified cosmetic composition additionally contains a UV absorbent, thereby forming a sunscreen cosmetic composition.

2 Claims, 1 Drawing Sheet

OIL-IN-WATER EMULSION COMPOSITION

CROSS REFERENCE TO RELATED APPLICATIONS

This application relates to and claims priority from PCT/JP2010/055367 filed Mar. 26, 2010, the entire contents of which are incorporated herein by reference, which in turn claims priority from JP 2010-070278 filed Mar. 25, 2010 and JP 2009-070278 filed Mar. 25, 2009.

FIGURE SELECTED FOR PUBLICATION

FIG. 1.

BACKGROUND OF THE INVENTION

1. Field of the Invention

The present invention relates to a base for cosmetic composition which provides moistness at the time of application and excellent water resistance after application, and a skin care cosmetic composition using the base, in particular, a sunscreen cosmetic composition.

2. Description of the Related Art

An oil-in-water emulsion that has been conventionally used as a base for various cosmetic compositions has good feeling of use with moistness. However, it is disadvantageous in that water resistance is not satisfactory.

In an attempt to improve the water resistance of an oil-in-water emulsion cosmetic composition, it is disclosed in Patent Document 1, for example, a makeup cosmetic composition containing an α-monoalkyl glyceryl ether, waxes and a silicone oil and having an addition amount of the silicone oil in an oil phase within a specific range and also including hydrophobicized powder to improve water resistance so that makeup retention properties are improved.

Further, in Patent Document 2, an oil-in-water emulsion cosmetic composition obtained by adding zinc oxide, a crosslinked acrylic copolymer, a nonionic or an anionic surfactant having an HLB of 10 or more, water, and a silicone oil and dispersing the zinc oxide into an oil phase is disclosed, and it is described that storage stability, transparency after use, and water resistance are improved.

Meanwhile, there has been a problem that, when a high amount of alcohol is added to an oil-in-water emulsion base, the emulsified particles are disrupted so that a sufficiently stable base may not be easily obtained. It is disclosed in Patent Document 3 an oil-in-alcohol water emulsion composition containing an oil, 50% by weight or more of a lower alcohol, water, and an emulsifying agent including one or more types of polyether-modified silicones represented by the following general formula:

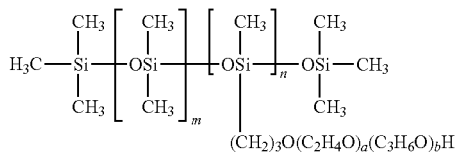

(CH₂)₃O(C₂H₄O)ₐ(C₃H₆O)ᵦH (wherein m is an integer of 50 to 1,000, n is an integer of 1 to 40, a is an integer of 5 to 50, and b is an integer of 5 to 50), characterized in that substantially no other surfactant is contained as an emulsifying agent. It is disclosed that the composition can provide hair with shine, softness, and moistness and it also has an effect of enabling easier combing.

However, as a great amount of a lower alcohol is contained in the composition disclosed in Patent Document 3, it was difficult to apply the composition to a general skin care base.

PRIOR ART PUBLICATIONS

Patent Document

Patent Document 1: JP-A No. 2002-308730
Patent Document 2: JP-A No. 2005-272389
Patent Document 3: WO97/002888

ASPECTS AND SUMMARY OF THE INVENTION

Problem to be Solved by the Invention

An object of the invention is to provide an oil-in-water emulsion base which is stable even when much ethanol is blended therein (provided that, it is 50% by mass or less) and exhibits excellent water resistance after being applied to the skin or the like.

Means for Solving Problem

The inventors of the invention extensively studied to solve the problems described above, and as a result found that the problems can be solved by providing an oil-in-water emulsion by adding 5 to 50% by mass of ethanol while using a polyether-modified silicone having an HLB(Si) of 5 to 10 as a surfactant and also adding a specific amount of a hydrophilic thickening agent and a polyol, and completed the invention accordingly.

The HLB(Si) described herein indicates a value obtained by the following equation.

$$\frac{\text{Molecular weight of polyoxyethylene}\,(POE)\,\text{and polyoxypropylene}\,(POP)}{\text{Molecular weight}} \times 20$$

Specifically, it is provided by the invention an oil-in-water emulsion cosmetic composition characterized by containing:
(A) 0.1-10% by mass of a polyether-modified silicone having an HLB(Si) of 5-10,
(B) 5-50% by mass or less of ethanol,
(C) 0.01-3% by mass of a hydrophilic thickening agent, and
(D) 0.1-15% by mass or more of a polyol.

Effect of the Invention

As an emulsion cosmetic composition of the invention is an oil-in-water emulsion in which a great amount of ethanol is added, a moist feeling of use can be obtained. Meanwhile, after being applied to the skin or the like, as the composition undergoes a phase inversion to a water-in-oil type in accordance with evaporation of ethanol, excellent water resistance can be exhibited.

Further, when an UV absorbent is added to the emulsion cosmetic composition of the invention as a base, an excellent UV screening effect can be obtained in addition to the water resistance.

The above, and other aspects, features and advantages of the present invention will become apparent from the following description read in conjunction with the accompanying drawings, in which like reference numerals designate the same elements.

DETAILED DESCRIPTION OF THE PREFERRED EMBODIMENTS

Modes for Carrying Out the Invention

Figure 1:
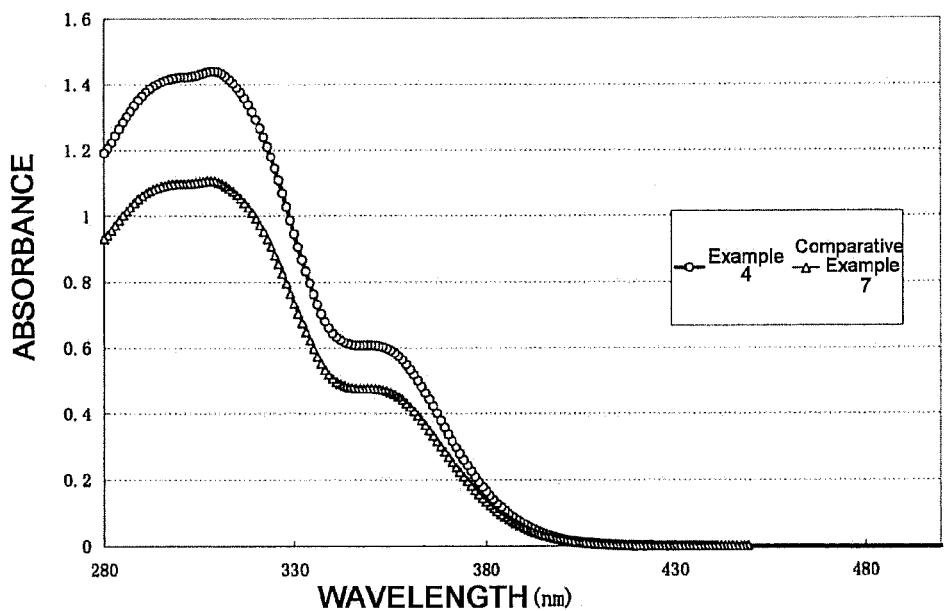
FIG. 1 is a graph illustrating the comparison of an UV screening effect between Example 4 and Comparative example 7.

A polyether-modified silicone (component A) in the oil-in-water emulsion cosmetic composition of the invention is selected from those having an HLB(Si) of 5-10, preferably 5-9.

According to the invention, the polyether-modified silicone having molecular weight of 50,000 or more and a hydrophilic group selected from polyoxyethylene (POE) and polyoxypropylene (POP) is preferably used.

In particular, the polyether-modified silicone represented by the following formula is preferable.

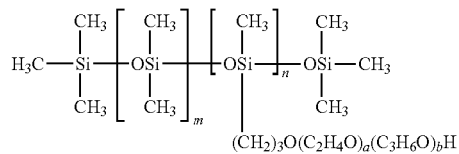

In the formula above, m is between 50 and 1000, preferably between 150 and 1000, and n is between 1 and 40. When m is less than 50 and n is less than 1, emulsion stability is insufficient. On the other hand, when m is more than 1,000 and n is more than 40, the composition obtained has a sticky feeling. Further, m:n is preferably between 200:1 and 5:1, and particularly preferably between 60:1 and 15:1.

Further, "a" is between 5 and 50 and "b" is between 5 and 50. Content of the polyoxyalkylene group in the molecule is not specifically limited, but the content of the polyoxyalkylene group is preferably more than 20% by weight in the total molecular weight.

The polyether-modified silicone represented by the formula above has been used as a surfactant for an oil-in-alcohol emulsion containing ethanol in an amount of 50% or more or for a water-in-oil emulsion (see, for example, WO97/002888 and JP-A No. Hei 10-306020). However, it has never been known before that the polyether-modified silicone is used in an oil-in-water emulsion containing a little amount of alcohol.

The invention is the first to use the polyether-modified silicone having an HLB(Si) of 10 or less, preferably 9 or less, as a surfactant for an oil-in-water emulsion. By controlling the addition amount of ethanol and adding a hydrophilic thickening agent, an oil-in-water emulsion is stably formed in a preparation, but after being applied to the skin or the like, it undergoes phase inversion to form water-in-oil type to exhibit excellent water resistance.

According to the invention, the addition amount of the polyether-modified silicone (component A) is 0.1-10% by mass, preferably 0.1-5% by mass, and more preferably 0.1-3% by mass. When the addition amount is less than 0.1% by mass or more than 10% by mass, a stable oil-in-water emulsion may not be obtained.

The emulsion cosmetic composition of the invention contains 5% by mass or more of ethanol (component B) as an essential component. The addition amount of ethanol is 5-50% by mass, preferably 8-50% by mass, and more preferably 8-40% by mass. When the addition amount is less than 5% by mass, a stable oil-in-water emulsion may not be obtained.

The emulsion cosmetic composition of the invention also contains a hydrophilic thickening agent (component C) as an essential component.

According to the invention, it was found that a stable emulsion cannot be obtained if only the polyether-modified silicone having an HLB(Si) of 10 or less, which has been conventionally used for a water-in-oil emulsion, is replaced with a surfactant generally used for an oil-in-water emulsion. Instead, it was found that a stable oil-in-water emulsion is formed by adding 5% by mass or more of ethanol and a hydrophilic thickening agent.

The hydrophilic thickening agent used in the invention is not specifically limited if it is commonly used for cosmetics. Examples thereof include a naturally-occurring water soluble polymer, a semi-synthetic water soluble polymer, a synthetic water soluble polymer, and an inorganic water soluble polymer.

Specific examples of the naturally-occurring water soluble polymer include plant polymers, such as gum Arabic, tragacanth gum, galactan, guar gum, carob gum, karaya gum, carrageenan, pectin, agar, quince seed (marmelo), algae colloid (brown algae extract), starch (rice, corn, potato, wheat), and glycyrrhizic acid; microbial polymers, such as xanthan gum, dextran, succinoglucan, and pullulan; animal polymers, such as collagen, casein, albumin, and gelatin.

Examples of the semi-synthetic water soluble polymer include starch-type polymers, such as carboxy methyl starch, and methyl hydroxypropyl starch; cellulose-type polymers, such as methyl cellulose, nitro cellulose, ethyl cellulose, methyl hydroxypropyl cellulose, hydroxyethyl cellulose, sodium cellulose sulfate, hydroxypropyl cellulose, sodium carboxymethyl cellulose (CMC), crystalline cellulose, and cellulose powder; alginic acid-type polymers, such as sodium alginate, and propylene glycol alginate ester.

Examples of the synthetic water soluble polymer include vinyl polymers, such as polyvinyl alcohol, polyvinyl methyl ether, polyvinyl pyrrolidone, and carboxyvinyl polymer (carbomer); polyoxyethylene-type polymers, such as polyethylene glycol (molecular weight 1500, 4000, 6000); polyoxyethylene-polyoxypropylene copolymer-based polymer; acrylic polymers, such as sodium polyacrylate, polyethyl acrylate, polyacrylamide, and alkyl acrylate/methacrylate copolymer (trade name: PEMULEN TR-1); polyethyleneimine; and cationic polymers. Examples of the inorganic water soluble polymers include bentonite, AlMg silicate (trade name: VEEGUM), laponite, hectorite, and silicic anhydride.

The addition amount of the hydrophilic thickening agent (component C) in the emulsion cosmetic composition of the invention is 0.01-3% by mass, preferably 0.05-3% by mass, and more preferably 0.2-1% by mass. When the addition amount is less than 0.01% by mass, a stable emulsion may not be obtained. When it is added in an amount of more than 3% by mass, a heavy feeling may be obtained at the time of application.

The emulsion cosmetic composition of the invention also contains a polyol (component D) as an essential component.

By adding a polyol, transparency and stability of the oil-in-water emulsion can be further improved. For example, by adding a polyol, stability can be still maintained even when the addition amount of alcohol is lowered, thus alcoholic smell of a formulation obtained can be prevented.

The polyol used in the invention is not specifically limited if it is commonly used for cosmetics. Examples thereof include dynamite glycerin, 1,3-butylene glycol, dipropylene glycol, and propylene glycol. In particular, 1,3-butylene glycol can most efficiently improve the stability.

The addition amount of the polyol (component D) in the emulsion cosmetic composition of the invention is 0.1-15% by mass, preferably 1-10% by mass, and more preferably 3-7% by mass. When the addition amount is less than 1% by mass, a stable emulsion may not be obtained. When it is added in an amount of more than 15% by mass, a heavy feeling may be obtained at the time of application.

The emulsion cosmetic composition of the invention can be produced according to a method that is conventionally used for producing an emulsion. For example, by mixing components for forming an oil phase and adding an oil phase in which oil components and the polyether-modified silicone (component A) having an HLB(Si) of 5-10 are admixed with each other to an aqueous phase containing ethanol (component B), a hydrophilic thickening agent (component C), and polyol (component D) under stirring by using a homomixer, etc., the oil-in-water emulsion cosmetic composition of the invention can be obtained.

The oil-in-water emulsion cosmetic composition of the invention is characterized in that it provides a moist and fresh feeling of use at the time of application and forms a dermal film having excellent water resistance after application. As such, the emulsion cosmetic composition of the invention is suitable as a base for a skin care cosmetic composition or a makeup cosmetic composition.

For example, when an oil soluble UV absorbent is added to the emulsion cosmetic composition of the invention, a moist and fresh feeling is obtained at the time of application on the skin. Further, since a dermal film having water resistance is formed on the skin after the application, a strong protection against UV light is maintained. Further, even when used for a makeup cosmetic composition, a good makeup retention state can be maintained based on its excellent water resistance.

Therefore, the invention provides an oil-in-water emulsion cosmetic composition further containing an UV absorbent, in particular, a sunscreen cosmetic composition.

The UV absorbent added to the emulsion cosmetic composition of the invention is not limited to an oil-soluble or a water-soluble absorbent. It is not specifically limited if it is commonly used for cosmetics.

Examples thereof include methoxy cinnamic acid derivatives, diphenyl acrylic acid derivatives, salicylic acid derivatives, para-aminobenzoic acid derivatives, triazine derivatives, benzophenone derivatives, benzalmalonate derivatives, anthranyl derivatives, imidazoline derivatives, 4,4-diarylbutadiene derivatives, and phenylbenzimidazole derivatives. Specific examples include 2-ethylhexyl para-methoxy cinnamate, homosalate, octyl salicylate, oxybenzone, 4-t-butyl-4'-methoxy dibenzoylmethane, octyltriazone, bisethylhexyl phenol methoxyphenyltriazine, methylene bisbenzotriazolyl tetramethylbutyl phenol, 2-hydroxy-4-methoxy benzophenone, dihydroxy dimethoxy benzophenone, dihydroxy benzophenone, tetrahydroxy benzophenone, diethylamino hydroxybenzoyl hexyl benzoate, 2-cyano-3,3-diphenylacrylic acid-2'-ethylhexyl ester, polysilicone-15, drometrizole polysiloxane, and phenyl benzimidazole sulfonic acid. It may be used either singly or two or more appropriately selected, if necessary.

The addition amount of the UV absorbent added to the oil-in-water sunscreen cosmetic composition of the invention is 0.1-35% by mass, preferably 1-30% by mass, and more preferably 5-25% by mass.

The emulsion cosmetic composition of the invention may contain, in addition to the essential components A to D above and/or the UV absorbent, other components that are conventionally used for cosmetics, within the range that the effect of the invention is not impaired. Specific examples thereof include a moisturizer, an oily component, a buffering agent, a chelating agent, and preservatives.

EXAMPLES

Herein below, the invention is described in greater detail with reference to the following Examples, by which, however, the invention is not limited to the following Examples at all. Unless otherwise specifically indicated, the addition amount described in the following Examples, etc. is all in terms of % by mass.

Examples 1 to 3

The oil-in-water emulsion cosmetic composition was produced according to the composition given in Table 1 below. Consequently, an example in which an oil-in-water emulsion with stable and small emulsion particles is obtained is marked with "A", an example in which a composition with stable but large emulsion particles is obtained is marked with "B", an example in which the composition is emulsified but the emulsion particles are large and unstable is marked with "C", and an example in which no emulsion is obtained is marked with "D", and they are summarized together in Table 1.

As it is clearly shown in Table 1, the Comparative examples 1, 2, and 3 in which the addition amount of ethanol is less than 5% by mass and acrylic acid/alkyl acrylate (C10-30) copolymer is not added cannot yield an oil-in-water emulsion. On the other hand, from the Example 1 in which ethanol is added in an amount of 5% by mass or more and acrylic acid/alkyl acrylate (C10-30) copolymer is added, it was possible to obtain an oil-in-water emulsion. In addition, from Examples 2 to 5 in which 1,3-butylene glycol is added, a more stable oil-in-water emulsion was produced.

TABLE 1

|  | Comparative Example 1 | Comparative Example 2 | Comparative Example 3 |
|---|---|---|---|
| Ion exchange water | balance | balance | balance |
| Ethyl alcohol | 0 | 3 | 5 |
| 1,3-Butylene glycol | — | — | — |
| Carbomer | 0.15 | 0.15 | 0.15 |
| Acrylic acid/alkyl acrylate (C10-30) copolymer | — | — | — |

TABLE 1-continued

|  |  |  |  |
|---|---|---|---|
| TEA | 0.24 | 0.24 | 0.24 |
| PEG/PPG-19/19 Dimethicone (HLB(Si) = 7.7)*) | 1.5 | 1.5 | 1.5 |
| Cyclopentasiloxane**) | 1.5 | 1.5 | 1.5 |
| Cetyl ethylhexanoic acid | 3 | 3 | 3 |
| Ethylhexyl methoxy cinnamate | 7.5 | 7.5 | 7.5 |
| Polysilicone -15 | 5 | 5 | 5 |
| Diethylamino hydroxybenzoyl hexyl benzoate | 2 | 2 | 2 |
| Chelating agent | 0.02 | 0.02 | 0.02 |
| Phenoxy ethanol | 0.5 | 0.5 | 0.5 |
| Total | 100 | 100 | 100 |
| Emulsion stability | D | D | D |

|  | Example 1 | Example 2 | Example 3 | Example 4 | Example 5 |
|---|---|---|---|---|---|
| Ion exchange water | balance | balance | balance | balance | balance |
| Ethyl alcohol | 5 | 5 | 10 | 15 | 50 |
| 1,3-Butylene glycol | — | 5 | 5 | 5 | 5 |
| Carbomer | 0.15 | 0.15 | 0.15 | 0.15 | 0.15 |
| Acrylic acid/alkyl acrylate (C10-30)copolymer | 0.1 | 0.1 | 0.1 | 0.1 | 0.1 |
| TEA | 0.4 | 0.4 | 0.4 | 0.4 | 0.4 |
| PEG/PPG-19/19 Dimethicone (HLB(Si) = 7.7)*) | 1.5 | 1.5 | 1.5 | 1.5 | 1.5 |
| Cyclopentasiloxane**) | 1.5 | 1.5 | 1.5 | 1.5 | 1.5 |
| Cetyl ethylhexanoic acid | 3 | 3 | 3 | 3 | 3 |
| Ethylhexyl methoxy cinnamate | 7.5 | 7.5 | 7.5 | 7.5 | 7.5 |
| Polysilicone -15 | 5 | 5 | 5 | 5 | 5 |
| Diethylamino hydroxybenzoyl hexyl benzoate | 2 | 2 | 2 | 2 | 2 |
| Chelating agent | 0.02 | 0.02 | 0.02 | 0.02 | 0.02 |
| Phenoxy ethanol | 0.5 | 0.5 | 0.5 | 0.5 | 0.5 |
| Total | 100 | 100 | 100 | 100 | 100 |
| Emulsion stability | C | B | A | A | A |

*)**)Product name: BY11-030 (manufactured by Dow Corning Toray Silicone Co., Ltd.): contains 50% by mass of PEG/PPG-19/19 dimethicone and 50% by mass of cyclopentasiloxane.

PEG/PPG-19/19 dimethicone indicates polyether-momdified silicone having molecular weight of 55,000 as represented by the following formula:

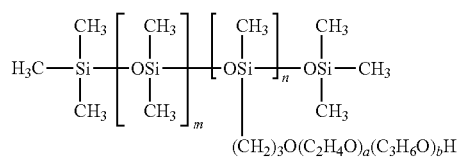

(in the formula, m = 400, n = 10, a = 19, and b = 19)

Comparative Examples 4 to 8

With respect to the composition of the Example 4, an emulsification test was carried out by using a composition in which the polyether-modified silicone having an HLB(Si) of 7.7 of the composition of the Example 4 is replaced with a various polyether-modified silicones described in Table 2 and a common O/W activating agent. Consequently, an example in which a oil-in-water emulsion with stable and small emulsion particles is obtained is marked with "o", an example in which a composition with stable but large emulsion particles is obtained is marked with "oΔ", an example in which the emulsion particles are large and unstable is marked with "Δ", and an example in which no emulsion is obtained is marked with "x", and they are summarized together in Table 2.

As a result, from the Comparative examples 4 to 6 in which the polyether-modified silicone having an HLB(Si) of less than 5 is used, it was impossible to obtain an oil-in-water emulsion having excellent stability. Meanwhile, from the Comparative example 7 in which polyoxyethylene (20) polyoxypropylene (8) cetyl ether, which is a representative O/W activating agent with an HLB(Si) of 10 or more, is used, an oil-in-water emulsion having excellent stability can be obtained.

TABLE 2

|  | Example 4 | Comparative Example 4 | Comparative Example 5 | Comparative Example 6 | Comparative Example 7 |
|---|---|---|---|---|---|
| Ion exchange water | balance | balance | balance | balance | balance |
| Ethyl alcohol | 15 | 15 | 15 | 15 | 15 |
| 1,3-Butylene glycol | 5 | 5 | 5 | 5 | 5 |
| Carbomer | 0.15 | 0.15 | 0.15 | 0.15 | 0.15 |
| Acrylic acid/alkyl acrylate (C10-30) copolymer | 0.1 | 0.1 | 0.1 | 0.1 | 0.1 |

TABLE 2-continued

| | Example 4 | Comparative Example 4 | Comparative Example 5 | Comparative Example 6 | Comparative Example 7 |
|---|---|---|---|---|---|
| TEA | 0.4 | 0.4 | 0.4 | 0.4 | 0.4 |
| PEG/PPG-19/19 Dimethicone (HLB(Si) = 7.7) | 1.5 | — | — | — | — |
| PEG-10 Dimethicone (HLB(Si) = 4.5) | — | 1.5 | — | — | — |
| PEG-9 Polydimethylsiloxy ethyl dimethicone (HLB(Si) = 4) | — | — | 1.5 | — | — |
| Luaryl PEG-9 polydimethylsiloxy ethyl dimethicone (HLB(Si) = 3) | — | — | — | 1.5 | — |
| Polyoxyethylene (20) polyoxypropylene (8) cetyl ether (HLB = 12.5) | — | — | — | — | 1.5 |
| Cyclopentasiloxane | 1.5 | 1.5 | 1.5 | 1.5 | 1.5 |
| Cetyl ethylhexanoic acid | 3 | 3 | 3 | 3 | 3 |
| Ethylhexyl methoxy cinnamate | 7.5 | 7.5 | 7.5 | 7.5 | 7.5 |
| Polysilicone -15 | 5 | 5 | 5 | 5 | 5 |
| Diethylamino hydroxybenzoyl hexyl benzoate | 2 | 2 | 2 | 2 | 2 |
| Chelating agent | 0.02 | 0.02 | 0.02 | 0.02 | 0.02 |
| Phenoxy ethanol | 0.5 | 0.5 | 0.5 | 0.5 | 0.5 |
| Total | 100 | 100 | 100 | 100 | 100 |
| Emulsion stability | A | D | D | D | A |

UV Screening Effect: Example 4 and Comparative Example 7

A test was carried out to compare a UV screening effect and a water resisting effect of the UV screening effect between the Example 4 and the Comparative example 7. For the comparison of UV screening effect, 0.75 mg/cm$^2$ of the formulation (Example 4 or Comparative example 7) was evenly coated on a PMMA (methyl polymethacrylate) plate of which surface has been roughened and the absorbance was measured by using a spectrophotometer (trade name: U-4100, manufactured by Hitachi, Ltd.). In addition, for the comparison of water resisting effect, the formulation (Example 4 or Comparative example 7) was coated on a PMMA plate mentioned above and the absorbance was measured. After that, the plate was exposed to strong flow of water for 15 min. After sufficient drying, the absorbance was measured once again and the ratio of change in maximum absorbance wavelength of ethylhexyl methoxy cinnamate was calculated.

Figure 2:
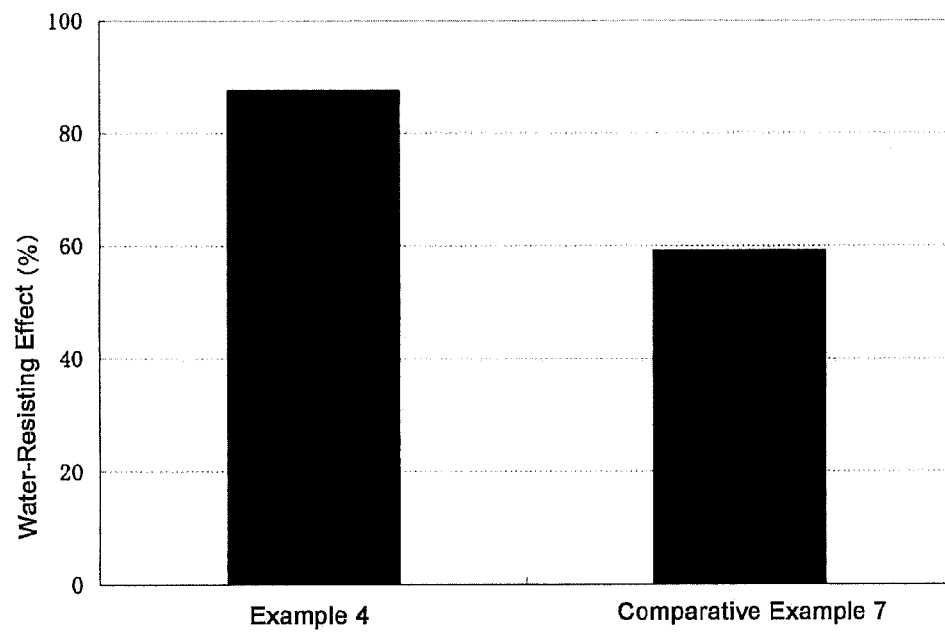
FIG. 2 is a graph illustrating the water resistance of a UV screening effect of Example 4 and Comparative example 7.

The results are depicted in FIG. 1 and FIG. 2. It was surprisingly found that the Example 4 exhibits a higher UV screening effect than the Comparative example 7 which uses the same absorbent as the Example 4. It was also found that the Example 4 exhibits a higher water resisting effect than the Comparative example 7.

Example 6

Sunscreen Emulsion

| | |
|---|---|
| Ion exchange water | Balance |
| Ethyl alcohol | 20 |
| Dipropylene glycol | 3 |
| Carbomer | 0.2 |
| Acrylic acid/alkyl acrylate (C10-30) copolymer | 0.2 |
| Aminomethyl propane diol | q.s. |
| Polyoxybutylene polyoxypropylene glycol | 2 |
| PEG/PPG-19/19 Dimethicone | 2 |
| Cyclopentasiloxane | 2 |
| Hydrogenated polyisobutene | 2 |
| Caprylyl methicone | 3 |
| Triethylhexanoin | 2 |
| Ethylhexyl methoxy cinnamate | 3 |
| Ocotocrylene | 3 |
| Bis ethylhexyloxyphenol methoxyphenyltriazine | 1 |
| Methylene bis benzotriazolyl tetramethylbutyl phenol | 1 |
| Chelating agent | q.s. |
| Ethyl paraben | q.s. |
| Fragrance | q.s. |

Example 7

Sunscreen Emulsion

| | |
|---|---|
| Ion exchange water | Balance |
| Ethyl alcohol | 20 |
| 1,3-Butylene glycol | 3 |
| Carbomer | 0.15 |
| Acrylic acid/alkyl acrylate (C10-30) copolymer | 0.15 |
| Aminomethyl propanol | q.s. |
| Polypropylene glycol | 3 |
| PEG/PPG-19/19Dimethicone | 1.5 |
| Dimethicone | 1.5 |
| Cyclopentasiloxane | 2 |
| Dimethyl polysiloxane | 2 |
| Pentaerythrityl tetraethylhexanoic acid | 3 |
| ethylhexyl methoxy cinnamate | 5 |
| Isododecane | 2 |
| t-Butylmethoxy dibenzoylmethane | 2 |
| Phenyl benzimidazole sulfonic acid | 2 |
| 2-Hydroxy4-methoxybenzophenone | 2 |
| Chelating agent | q.s. |
| Phenoxy ethanol | q.s. |

INDUSTRIAL APPLICABILITY

The oil-in-water emulsion cosmetic composition of the invention provides a moist feeling of use at the time of application, which is a characteristic of an oil-in-water emulsion, and after the application, it undergoes a phase inversion to a water-in-oil type to show excellent water resistance. As such, it can be used as a base for cosmetic composition which can provide both a favorable feeling of use and water resistance. For example, when it is blended with an UV absorbent, protection against UV light with excellent water resistance can be obtained, and when it is provided as a makeup cosmetic composition, makeup retention properties are improved.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

Having described at least one of the preferred embodiments of the present invention with reference to the accompanying drawings, it is to be understood that the invention is not limited to those precise embodiments, and that various changes, modifications, and adaptations may be effected therein by one skilled in the art without departing from the scope or spirit of the invention as defined in the appended claims.

The invention claimed is:

1. An oil-in-water emulsion cosmetic composition consisting essentially of:
   (A) 0.1-10% by mass of a polyether-modified silicone having an HLB(Si) of 5-7.7, represented by the following formula:

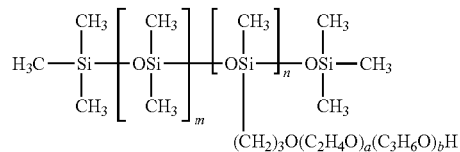

wherein "m" is an integer of 50 to 1,000, "n" is an integer of 1 to 40, "a" is an integer of 5 to 50, and "b" is an integer of 5 to 50;
   (B) 8-50% by mass of ethanol,
   (C) 0.01-3% by mass of a hydrophilic thickening agent, and
   (D) 0.1-15% by mass of a polyol,
   wherein, after application of the composition to a user's skin, evaporation of ethanol from the composition causes inversion to a water-in-oil emulsion further comprising 0.1 to 35% by mass of an UV absorbent, wherein the composition is a sunscreen.

2. An oil-in-water emulsion cosmetic composition according to claim 1, wherein the polyether-modified silicone is PEG/PPG-19/19 dimethicone.

* * * * *